(12) United States Patent
Xia et al.

(10) Patent No.: US 7,400,789 B2
(45) Date of Patent: Jul. 15, 2008

(54) METHOD, SYSTEM AND MODULE FOR MONITORING A POWER GENERATING SYSTEM

(75) Inventors: Hua Xia, Altamont, NY (US); Kung-Li Justin Deng, Waterford, NY (US); Kevin Thomas McCarthy, Troy, NY (US); Avinash Vinayak Taware, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/468,162

(22) Filed: Aug. 29, 2006

(65) Prior Publication Data
US 2007/0116401 A1     May 24, 2007

Related U.S. Application Data

(62) Division of application No. 11/284,595, filed on Nov. 22, 2005, now Pat. No. 7,151,872.

(51) Int. Cl.
*G02B 6/00* (2006.01)
(52) U.S. Cl. .......................... 385/12; 385/37
(58) Field of Classification Search ............. 385/12, 385/13, 37, 147
See application file for complete search history.

(56) References Cited

U.S. PATENT DOCUMENTS

| 2004/0245444 | A1 | 12/2004 | MacDougall |
| 2006/0139741 | A1 | 6/2006 | Chen et al. |
| 2006/0140559 | A1 | 6/2006 | Tsuda et al. |
| 2006/0215959 | A1* | 9/2006 | McCarthy et al. ............. 385/37 |

OTHER PUBLICATIONS

U.S. Appl. No. 11/086,055, filed Mar. 22, 2005, title: "Fiber Optic Sensing Device and Method of Making and Operating the Same".
U.S. Appl. No. 11/240,057, filed Sep. 30, 2005, title: "Fiber Optic Chemical Sensing Device, System, and Method".

* cited by examiner

*Primary Examiner*—Kevin S Wood
(74) *Attorney, Agent, or Firm*—Ann M. Agosti

(57) ABSTRACT

A sensing module positioned about an optical fiber cable having a long axis. The optical fiber includes a core that transmits light through the optical fiber cable. The sensing module includes a first short-period fiber grating positioned about the core. A second short-period fiber grating is positioned about the core and at a distance along the long axis with respect to the first short-period fiber grating. At least one of a long-aperiod fiber grating and a long-period fiber grating is positioned between the first short-period fiber grating and the second short-period fiber grating. A fiber cladding is positioned around the long-period grating and/or the long-aperiod grating of the sensing module. A sensing skin is positioned about the fiber cladding and includes a chemical gas active material.

7 Claims, 7 Drawing Sheets

METHOD, SYSTEM AND MODULE FOR MONITORING A POWER GENERATING SYSTEM

CROSS REFERENCE TO RELATED APPLICATIONS

This application is a Division of U.S. patent application Ser. No. 11/284,595 entitled "Method, System and Module for Monitoring a Power Generating System" filed Nov. 22, 2005, now U.S. Pat. No. 7,151,872 which is herein incorporated by reference

BACKGROUND OF THE INVENTION

This invention relates generally to power generating systems and, more particularly, to a method and system for emission control and combustion optimization in fossil fuel fired boilers with an array of fiber grating-based sensing modules.

In numerous industrial environments, a hydrocarbon fuel is burned in stationary combustors (e.g., boilers or furnaces) to produce heat to raise the temperature of a fluid, e.g., water. For example, the water is heated to generate steam, and this steam is then used to drive turbine generators that output electrical power. Such industrial combustors typically employ an array of many individual burner elements to combust the fuel. In addition, various means of combustion control, such as overfire air, staging air, reburning systems and selective non-catalytic reduction systems, can be employed to enhance combustion conditions and reduce emissions of oxides of nitrogen ($NO_x$) and carbon monoxide.

Emissions and efficiency are key performance metrics for industrial boilers that are often used for generation of process steam required for industries. Emissions and efficiency are important performance metrics for utility boilers, which are mainly used for power generation along with generation of process steam. Poor or non-uniform combustion leads to low availability, low peak steam/power generation, low efficiency and high emissions. Conventional industrial boiler and utility boiler controls are often based on data driven or empirical models with limited feedback from the boiler environment due to limited real-time, multi-point monitoring and sensing capabilities. Most sensing systems that are used to monitor $NO_x$, CO and temperature use single-point sensors that are typically placed in the boilers exhaust area. Often, gas sensing is ex-situ and extractive in nature.

For a combustion system, such as a multiple burner boiler furnace or a gas turbine combustor, to operate efficiently and to produce an acceptably complete combustion that generates byproducts falling within the limits imposed by environmental regulations and design constraints, all individual burners in the combustion system must operate cleanly and efficiently and all combustion modification systems must be properly balanced and adjusted. Emissions of $NO_x$, carbon monoxide (CO), mercury (Hg) and/or other byproducts generally are monitored to ensure compliance with environmental regulations and acceptable system operation. Such operating conditions and/or gas emissions can be monitored using sensors.

Due to non-uniform combustion, power generation oriented utility boilers or process steam generating industrial boilers tend to operate at lower efficiencies than the design limits, thus resulting in high operating and maintenance costs. In addition, limited sensing and actuation capabilities and limited real-time information regarding boiler condition leads to solutions that are not very effective for reducing emissions or improving efficiency. Many conventional industrial or utility boilers suffer in this context and provide only limited improvements in emission reduction and/or efficiency.

Conventional electric-based gas sensors operate at temperatures less than about 500° C. due to sensing material and/or device limitations. The reliability of conventional electric-based gas sensors has suffered from several problems. These gas sensors fail to operate when the environmental temperature is higher than the sensor's operating temperature. It is also difficult to predict the gas concentration due to the temperature-dependent nonlinear sensitivity characteristics. Additionally, electric-based gas sensors suffer from long-term stability or sensitivity degradation due to thermal effects on the electrical interfaces to supply power or transmitting signal. Further, they are not suitable for high-voltage and explosive environments. Finally, electric-based sensors are not suitable for multiple point gas sensing applications.

Solid-state semiconductor gas sensing technology generally performs better than the electrochemical gas sensing technology due to the use of a wide band-gap material that allows high temperature operation up to 500° C. Despite the drift due to the temperature-dependent resistivity at higher temperature, solid-state semiconductor gas sensors provide an acceptable performance as a point sensor. However, these devices also tend to fail at higher temperatures due to thermal effects on the electrical interfaces to supply power or a transmitting signal as well. Further, because the sensing performance varies significantly with environmental temperature, pressure variations and/or toxic gas variations, solid-state semiconductor gas sensors require a constant calibration to maintain accuracy.

There is no systematic method to adjust the air and fuel flows for reducing spatial variance of emissions at a boiler's exit to reduce stack emissions. Rather, conventional boiler combustion optimization procedures are primarily established using the boiler expert's domain knowledge. Data-driven models such as Neural Networks and Expert Systems lack the rigor and fidelity and thereby have limited impact on efficiency because these models are dependent on data quality and are prone to data noise and inaccuracies. Model-based optimization systems that incorporate the physics of the combustion system along with accurate and spatially dense data provided by a fiberoptic sensor array overcome the limitations of currently available boiler optimization products that rely on data limited in terms of availability, accuracy and spatial density due to the harsh environment of boiler systems and sensor capability limitations.

BRIEF DESCRIPTION OF THE INVENTION

In one aspect, the present invention provides a sensing module positioned about an optical fiber cable having a long axis. The optical fiber cable includes a core that transmits light through the optical fiber. The sensing module includes a first short-period fiber grating positioned about the core. A second short-period fiber grating is positioned about the core and at a distance along the long axis with respect to the first short-period fiber grating. At least one of a long-aperiod fiber grating and a long-period fiber grating is positioned between the first short-period fiber grating and the second short-period fiber grating. A fiber cladding is positioned about the long-aperiod fiber grating and/or the long-period fiber grating. A sensing skin having a chemical gas active material is positioned about the fiber cladding.

In another aspect, a system for monitoring operating conditions of a power generating system is provided. The system includes an optical fiber sensing cable that extends through at least a portion of the power generating system. The optical fiber sensing cable has a core. An array of sensing modules is positioned along the optical fiber sensing cable. Each sensing module includes a plurality of fiber gratings for monitoring at least one power generating system operating condition. A broadband light source emits a light through the fiber core. An optical coupler in communication with the light source transmits a portion of the light through the fiber core and a fiber grating structure reflects a portion of the light from the plurality of fiber gratings to a photodetector.

In another aspect, the present invention provides a method for monitoring operating conditions of a power generating system. The method includes providing a sensing system including an optical fiber sensing cable that extends at least partially with respect to the power generating system. The optical fiber sensing cable has a fiber core that extends along a long axis of the optical fiber sensing cable. An array of multi-functional sensing modules each is positioned about the fiber core at a spatial location of the power generating system. A modified fiber cladding including a sensing material with chemical gas sensitivity surrounds each multi-functional sensing module. A broadband light is propagated through the fiber core. At least one operating condition is detected at least one spatial location. A light signal is reflected by at least one multi-functional sensing module or transmitted to a near infrared photodetector. Within the photodetector, the light signal is processed and a corresponding electrical signal is communicated to a computer interfaced with the sensing system.

DETAILED DESCRIPTION OF THE INVENTION

The present invention provides a sensing method and system for monitoring operating conditions and/parameters of a power generating system, such as, without limitation, a fossil fuel fired boiler, a gas turbine and a steam turbine. As an exemplary embodiment, the invention will be described in the context of a boiler system. The sensing method and system detect the presence of gases and/or the concentration of the gases produced a combustion process within the boiler furnace, as well as other operating conditions and/or parameters including, without limitation, temperature, heat flux and/or pressure. The sensing method and system includes an array of sensing modules each positioned at a spatial location within the power generating system to monitor operating conditions and/or parameters, such as combustion conditions that include emissions, temperature and/or pressure. The sensing method and system also includes using the detected information to make adjustments to boiler system parameters, such as burner air to fuel ratio, total airflow and fuel flow to the boiler, to yield optimized boiler performance objectives as indicated by the in-furnace sensors. Optimized performance includes, for example CO and $NO_x$ emissions, reduced byproducts emissions, increased efficiency, increased power output, improved superheat temperature profile and/or reduced opacity. Boiler system adjustments include, for example, adjusting or tuning mill (a set of burners) level coal and air flow, individual burner fuel to air ratio, overfire airflows and other furnace input settings such as total airflow and total fuel flow to the boiler plant.

By implementing multi-point, in-situ gas sensors that operate closer to combustion areas, i.e. upstream of exhaust, the effectiveness of model-based combustion optimization methods can be greatly improved, thus improving boiler efficiency and reducing emissions. Principally, the accuracy of empirical models such as Computational Fluid Dynamics based models or data driven models such as Neural Networks used by such optimization methods is greatly improved by the improved accuracy and spatially more dense information provided by the fiber optic based multi-point, multi-parameter sensing system.

Figure 1:
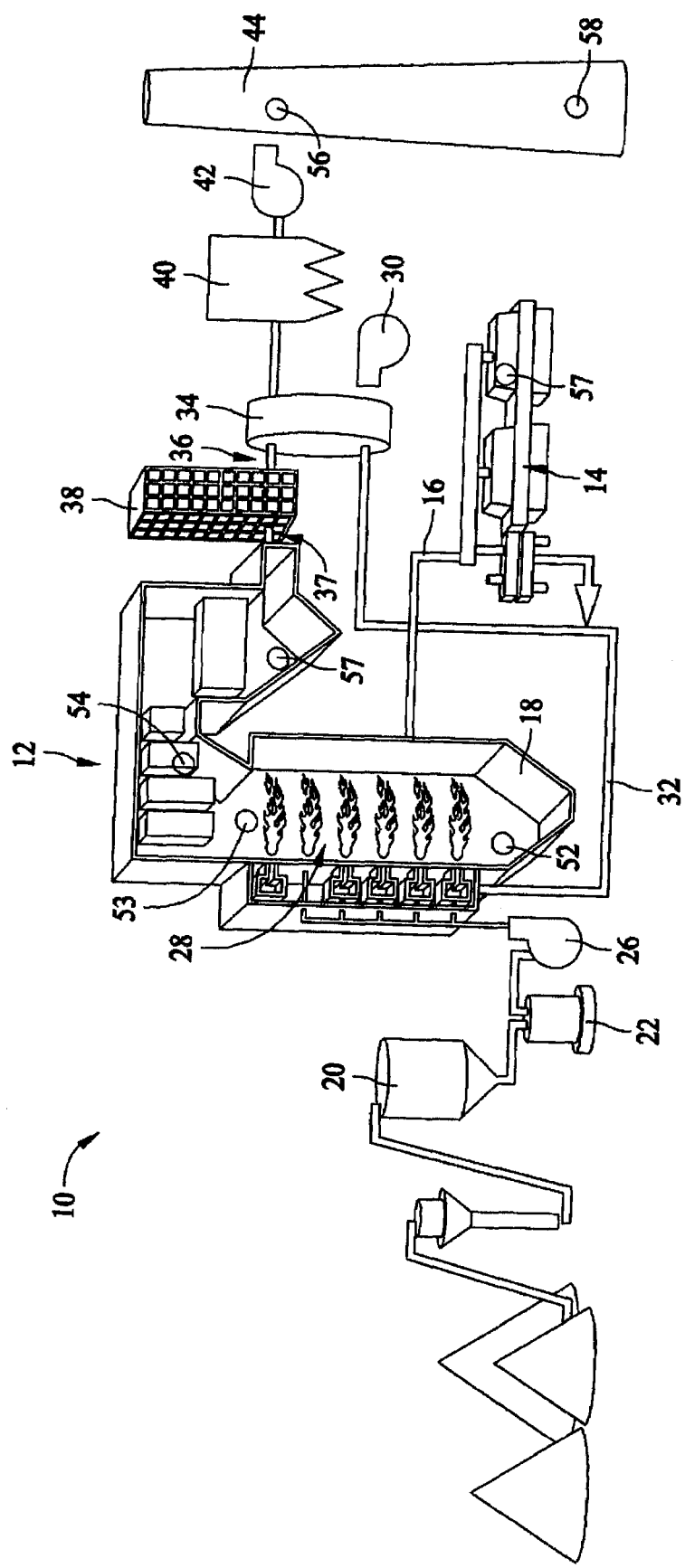
FIG. 1 is schematic view of a power generating system that includes a fossil fuel fired boiler.

A schematic view of a power generating system 10 is shown in FIG. 1. In one embodiment, power generating system 10 includes a boiler 12 coupled to a steam turbine-generator 14. Steam is produced in boiler 12 and flows through steam pipe 16 to generator 14. Boiler 12 burns a fossil fuel, such as coal, in a boiler furnace 18 which produces heat to convert water into steam used to drive generator 14. In alternative embodiments, the fossil fuel burned in boiler 12 can include oil or natural gas. Crushed coal is stored in a silo 20 and is further ground or pulverized into fine particulates by a pulverizer or mill 22. A coal feeder (not shown) adjusts the flow of coal from coal silo 20 into mill 22. An air source, for example, fan 26 is used to convey the coal particles to furnace 18 where the coal is burned by burners 28. The air used to convey the coal particles from mill 22 to burners 28 is referred to as primary air. A second fan 30 supplies secondary air to burners 28 through air conduit and a windbox 32. The secondary air is heated by passing through a regenerative heat exchanger 34 located in a boiler exhaust line 36. The combustion gas exits boiler 18 at an exit 37.

In one embodiment, the combustion gas is directed through boiler exhaust line 36 through a selective catalyst reduction device ("SCR") 38 to reduce $NO_x$ contained in the combustion gas. Within SCR 38, $NO_x$ is reduced to nitrogen and oxygen. An electrostatic precipitator ("ESP") 40 is positioned downstream of SCR 38. The combustion gas enters ESP 40. Within ESP 40, a portion of a particulate matter contained within the combustion gas is removed or precipitated out of the combustion gas as the combustion gas is directed through ESP 40. A fan 42 directs the filtered combustion gas through a suitable exhaust pipe or chimney 44 to exhaust gases generated during the combustion process from power generating system 10.

Figure 2:
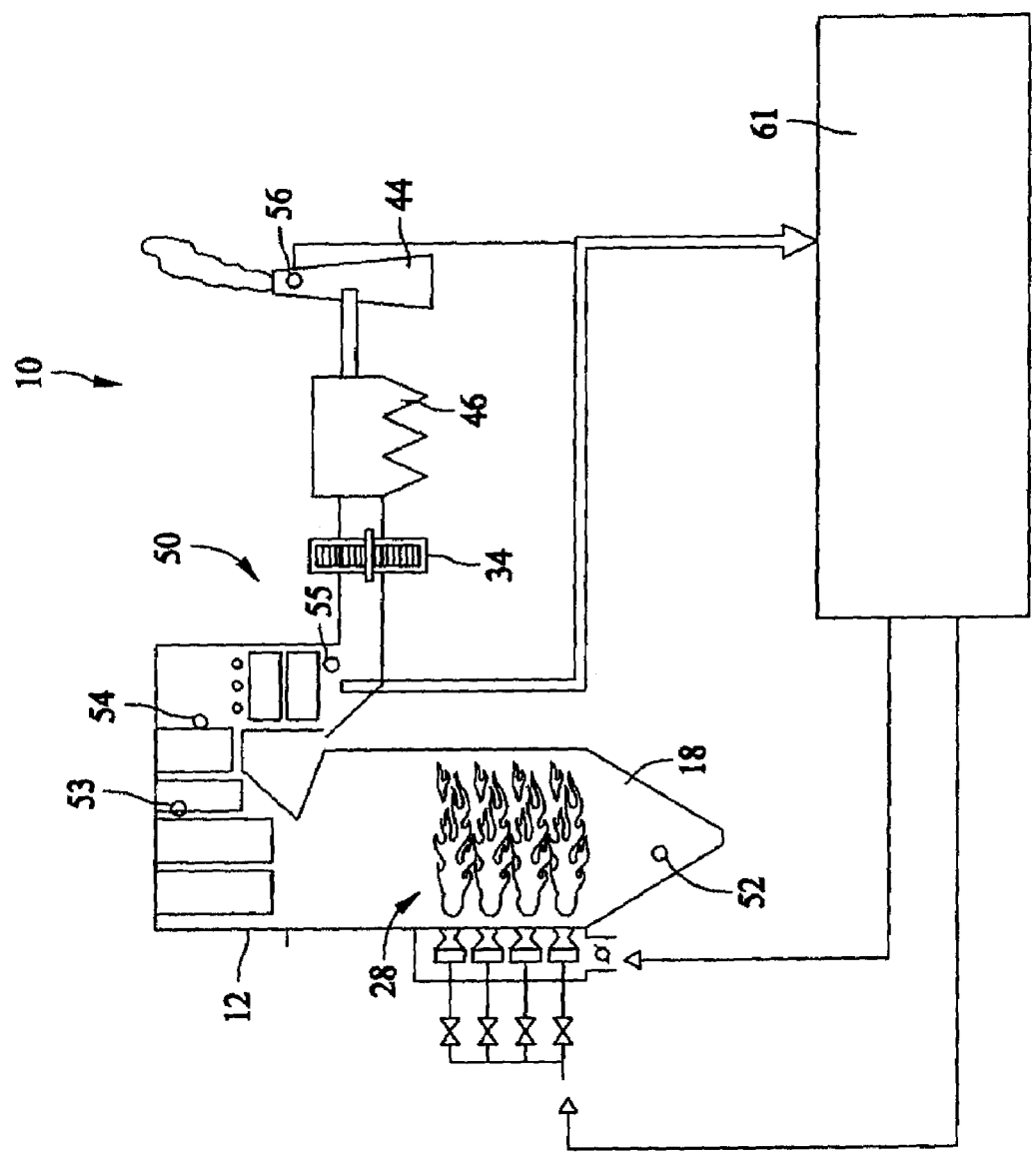
FIG. 2 is a schematic view of the fossil fuel fired boiler shown in FIG. 1.

Referring also to FIG. 2, boiler furnace 18 includes an array 50 of multi-functional sensing modules 52, 53, 54, 55 and/or 56 located with respect to at least a portion of power generating system 10. In one embodiment, array 50 is positioned with respect power generating system 10 and, more particularly, with respect to boiler 12. For example, at least one multi-functional sensing module 52, 53, 54, 55 and/or 56, as discussed in greater detail below, is positioned at a spatial location within boiler furnace 18, with respect to exit 37 of boiler furnace 18, with respect to generator 14 and/or within exhaust chimney 44. Multi-functional sensing modules 52, 53, 54, 55 and/or 56 monitor the combustion process occurring within boiler furnace 18 as well as the constituents of the combustion gas generated during the combustion process and exhausted from power generating system 10. Array 50 provides directly correlated and indirectly correlated (relative) measurements. Combustion quality indications can be obtained from absolute measurement, relative measurement and drawing from analysis of fluctuations in combustion quality indicator sensor signals. Each multi-functional sensing module 52, 53, 54, 55 and 56 monitors the combustion process conditions and/or parameters at a spatial location including, without limitation, optical radiation, temperature, vibrations, carbon monoxide (CO) emission, carbon dioxide ($CO_2$) emission, $NO_x$ emission, total hydrocarbons (THC) emission, volatile organic compounds (VOC) emission, sulfur dioxide ($SO_2$) emission, heat flux, radiance, opacity, emissivity, moisture, hydroxyl radicals (OH) emission, sulfur trioxide ($SO_3$) emission and/or particulate matter emission.

Referring further to FIGS. 3-6, in one embodiment, a sensing system 60 includes array 50 to monitor the operating conditions and/or parameters of power generation system 10 and, more particularly, the operating conditions and/or parameters of boiler 12. Such operating conditions and/or parameters include, but are not limited to, internal temperatures, pressures, seismic variations and/or the presence and concentration levels of chemical combustion gases generated within boiler 12 and emitted from power generating system 10. A control system 61, as shown in FIG. 2, is in operating control communication with sensing system 60 to receive signals generated as a result of sensor detection and to control the operation of boiler 12 to reduce emissions and increase boiler efficiency by controlling burner fuel to air ratios and/or total airflow to the boiler system. In one embodiment, efficiency is optimized by reducing fouling and/or slag, for example by using the sensed temperatures, strains or pressures to detect a level of slag and/or fouling.

In one embodiment, sensing system 60 includes an optical fiber cable 62 that is positioned with respect to and extends along the components of power generating system 10. For example, optical fiber cable 62 extends through boiler 12 towards exhaust chimney 44. As shown in FIG. 4, optical fiber cable 62 includes a central fiber core 64 formed of a doped silica that extends along a long axis 63 and having a diameter of about 5 microns to about 9 microns. In a particular embodiment, fiber cable 64 includes a periodic modulated refractive index structure. A fiber cladding 66 circumferentially covers fiber core 64 and has an outer diameter of about 125 microns made from pure silica. In one embodiment, fiber cladding 66 is configured to act as a waveguide for light propagation through fiber core 64. Broadband light source 70, shown in FIG. 3, is positioned in light emitting communication with optical fiber cable 62 and emits a near infrared light that propagates through fiber core 64.

Figure 3:
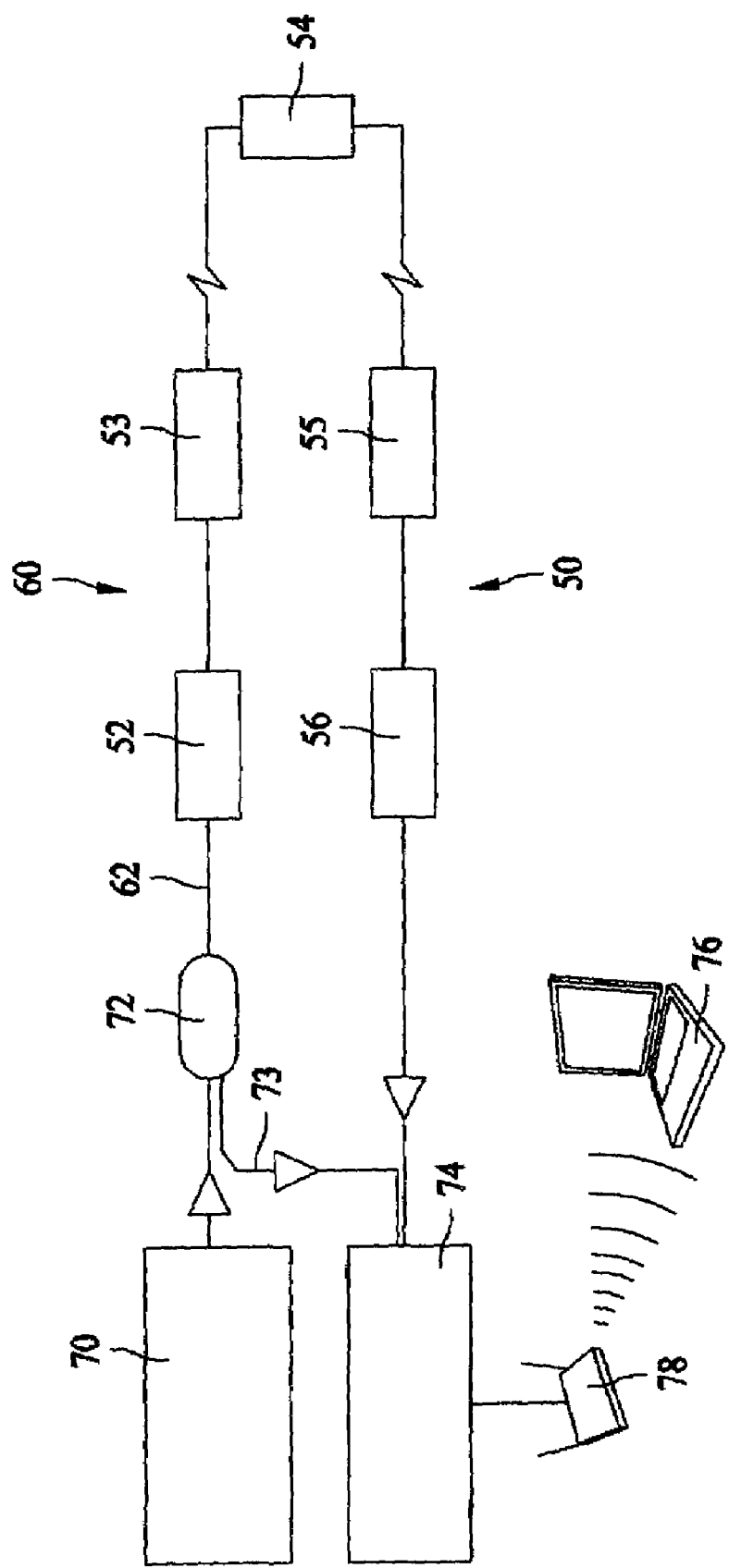
FIG. 3 is a schematic view of a sensing system for monitoring the operating conditions and/or parameters of the power generating system.
Figure 4:
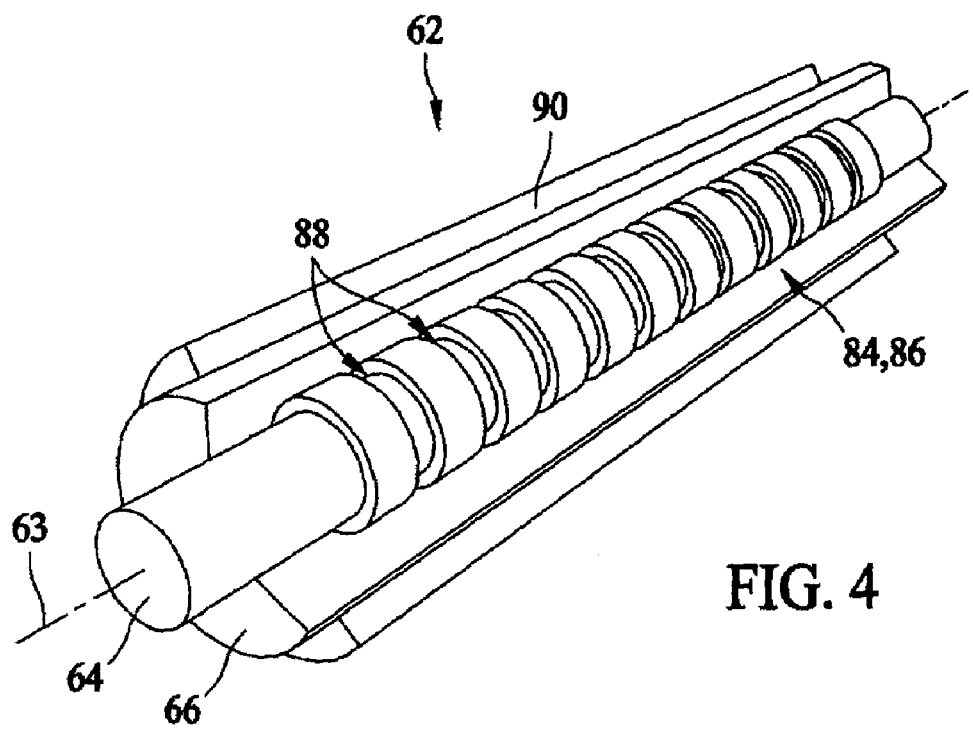
FIG. 4 is a perspective view of a sensing module for the sensing system schematically shown in FIG. 3.

An optical coupler or circulator 72, schematically shown in FIG. 3, is in light communication with light source 70. Optical coupler 72 receives the light transmitted from light source 70 and transmits a portion of the light through fiber core 64 of optical fiber cable 62 and a fiber grating structure reflects and/or redirects a portion of the light through a second optical fiber 73 to a photodetector 74 positioned downstream.

Figure 5:
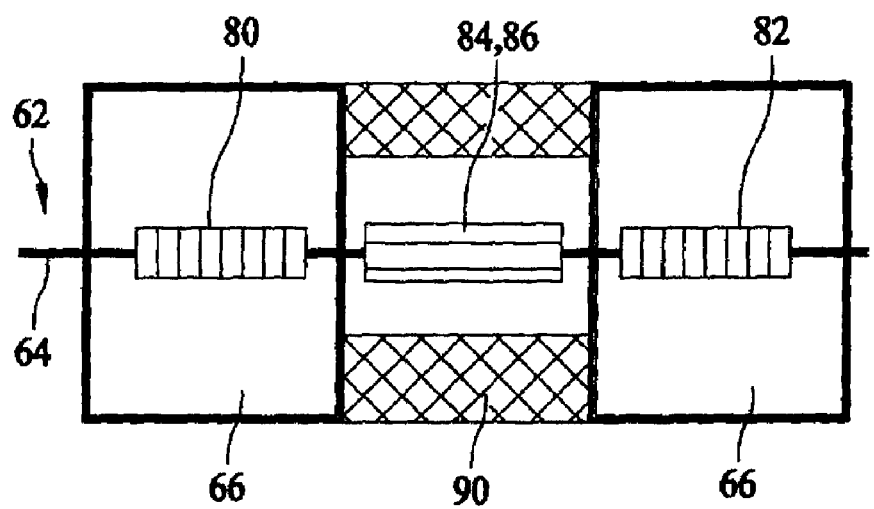
FIG. 5 is a schematic view of a sensing module for the sensing system schematically shown in FIG. 3.

In one embodiment, sensing system 60 includes array 50 of multi-functional sensing modules 52, 53, 54, 55 and/or 56 positioned along optical fiber cable 62 extending through power generating system 10. Referring to FIGS. 3-5, in a particular embodiment, array 50 includes multi-functional sensing module 52 positioned within boiler furnace 18 to monitor fouling and/or slag by using temperature, strain and/or pressure sensing. Additionally, multi-functional sensing modules 53, 54 and/or 55 are positioned within boiler furnace 18 at spatial locations, such as at exit 37 of boiler 12, to monitor the presence and/or concentration of constituents of the combustion gas, such as CO, $O_2$, $NO_x$ and/or $H_2$ for combustion control and optimization. Further, multi-functional sensing module 56 is positioned with respect to exhaust chimney 44 to monitor the presence and/or concentration of constituents of the combustion gas downstream from boiler 12. Additional multi-functional sensing modules, such as multi-functional sensing module 57 and/or 58, are positioned with respect to power generating system 10 to monitor the operating conditions and/or parameters for power generating system 10, as desired.

Although array 50 shown in FIGS. 2 and 3 includes five multi-functional sensing modules 52, 53, 54, 55 and/or 56, it is apparent to those skilled in the art and guided by the teachings herein provided that in alternative embodiments, array 50 includes any suitable number of multi-functional sensing modules, either less than five or greater than five. In an alternative embodiment, in addition to multi-functional sensing modules 52, 53, 54, 55 and/or 56, array 50 includes multi-functional sensing module 57 positioned with respect to generator 14 to monitor the presence and/or concentration of CO and/or the temperature within generator 14, which may exceed 1000° C., and/or multi-functional sensing module 58 positioned with respect to exhaust chimney 44 to monitor the emission of exhaust gas including, without limitation, CO, $CO_2$ and/or $H_2S$ in order to adhere to governmental and/or environmental safety standards and/or parameters.

As shown in FIG. 3, the light is transmitted or propagated through fiber core 64, with multi-functional sensing module 52, 53, 54, 55 and/or 56 positioned about fiber core 64, and into photodetector 74. As the light is transmitted through multi-functional sensing module 52, 53, 54, 55 and/or 56, light having a selected wavelength is reflected by the fiber grating structure. The reflected light wavelength corresponds to at least one operating condition and/or parameter, such as CO, $NO_x$ and/or temperature, detected by multi-functional sensing module 52, 53, 54, 55 and/or 56. Multi-functional sensing module 52, 53, 54, 55 and/or 56 reflects and/or redirects the light to generate a light signal that depends upon the measurands. The light signal generated by multi-functional sensing module 52, 53, 54, 55 and/or 56 is transmitted to photodetector 74 wherein the light signal is processed and/or transmitted to a computer 76 interfaced and/or communicating with sensing system 60. For example, in one embodiment, a wireless interface 78 transmits electrical signals to computer 76 generated by photodetector 74 in response to light signals received from multi-functional sensing module 52, 53, 54, 55 and/or 56.

Figure 8:
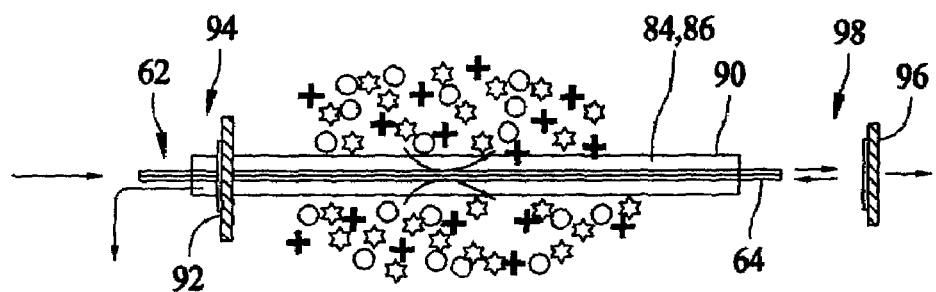
FIG. 8 is a schematic view of an evanescent wave field profile and its coupling back to fundamental mode in the gas sensing grating through the sensing module shown in FIG. 5.

Referring to FIGS. 4, 5 and 8, in one embodiment, multi-functional sensing module 52, 53, 54, 55 and/or 56 has a length along long axis 63 of optical fiber cable 62 of about 20 millimeters to about 50 millimeters. In this embodiment, multi-functional sensing module 52, 53, 54, 55 and/or 56 includes two short-period fiber gratings 80, 82. At least one long-aperiod fiber grating (LAG) 84 and/or at least one long-period fiber grating (LPG) 86 is positioned between short-period fiber gratings 80, 82, and generally indicated in FIGS. 4, 5 and 8 as sensing element reference number 84/86. In one embodiment, LAG 84 and/or LPG 86 have a modulation along long axis 63 with a pitch size of about 100 microns to about 600 microns. LAG 84 and/or LPG 86 are configured to effectively shed a fundamental mode energy to fiber cladding 66 and radiation modes. First short-period fiber grating 80, second short-period fiber grating 82, LAG 84 and LPG 86 each has a length along long axis 63 of about 5 millimeters to about 30 millimeters. Further, a spacing 88 is defined between adjacent fiber gratings 80, 82, 84 and/or 86 of about 10 millimeters to about 50 millimeters.

Multi-functional sensing module 52, 53, 54, 55 and/or 56 includes a modified cladding or sensing skin 90 positioned about fiber cladding 66, as shown in FIG. 4. Sensing skin 90 is configured to effectively assist the coupling of fiber cladding 66 to the fundamental mode. Sensing skin 90 includes a sensing or chemical gas active material including at least one base material, such as $SnO_2$, $WO_x$, $TiO_2$, $Fe_2O_3$ and $Ga_2O_3$, that is doped with material nanoparticles, such as Pd, Pt, Au, Ag, Ni and CuO particles. The material nanoparticles have a diameter of about 5 nm to about 10 nm. In one embodiments, sensing skin 90 includes a sensing material with chemical gas sensitivity, which is sensitive and/or activated by interactions with a chemical gas. In a particular embodiment, multi-functional sensing module 52, 53, 54, 55 and/or 56 of array 50 is configured to detect the presences of CO, $NO_x$, $O_2$, $H_2$ and or $H_2S$. It is apparent to those skilled in the art and guided nu the teachings herein provided that sensing skin 90 can be fabricated using a doping process to sense or detect any desired chemical gas.

In one embodiment, sensing skin 90 includes a sensing material that is sensitive to the presence of CO. For example, sensing skin 90 includes a nano-Pt/$SnO_2$ sensing material and/or a nano-Pd/Au/$Ga_2O_3$ sensing material. In this embodiment, adsorbed oxygen and surface oxygen vacancies act as electron or hole trap states. The variations in oxygen vacancies result in a strong optical absorption, thereby varying the refractive index of the coated sensing material, and altering the light coupling between the fundamental mode and cladding mode, and the coupling between the cladding mode and radiation mode in the long-aperiod/period grating cladding area. This enables an observable change in both transmission and reflection, and eventually leads to the identification of the CO gas adsorbed. Simultaneous mapping of CO gas concentration and localized temperature value is obtained with the same sensing module using the multi-functional and differential interrogation configuration of the present invention.

In a particular embodiment for incorporation into sensing system 60 at a temperature of less than about 400° C. (about 750° F.), sensing skin 90 includes a base material of $SnO_2$. The $SnO_2$ base material is doped with suitable material nanoparticles of Pd, Pt, Au, Ag and/or Ni. The nanoparticles have a diameter of about 5 nm to about 10 nm. In this embodiment, sensing skin 90 is prepared using a Sol-gel process or a sputtering process. It is apparent to those skilled in the art and guided by the teachings herein provided that any suitable process can be used to prepare sensing skin 90. After sensing skin 90 is prepared, sensing skin 90 is annealed in an $Ar^+$ environment for about 2 hours at 600° C.

In an alternative embodiment for incorporation into sensing system 60 at a temperature of at least about 400° C. (about 750° F.), sensing skin 90 includes a base material of $Ga_2O_3$. The $Ga_2O_3$ base material is doped with suitable material nanoparticles of Pd, Pt, Au, Ag and/or Ni. The nanoparticles have a diameter of about 5 nm to about 10 nm. In this embodiment, sensing skin 90 is prepared using any suitable process known to those skilled in the art and guided by the teachings herein provided, such as a Sol-gel process or a sputtering process. After sensing skin 90 is prepared, sensing skin 90 is annealed in an $Ar^+$ environment for about 6 hours at 1000° C. The sensing material fabricated using these processes provides adequate response and is capable of surviving prolonged operation at an elevated temperature in a highly corrosive environment such as that of a boiler furnace and exhaust area.

Figure 6:
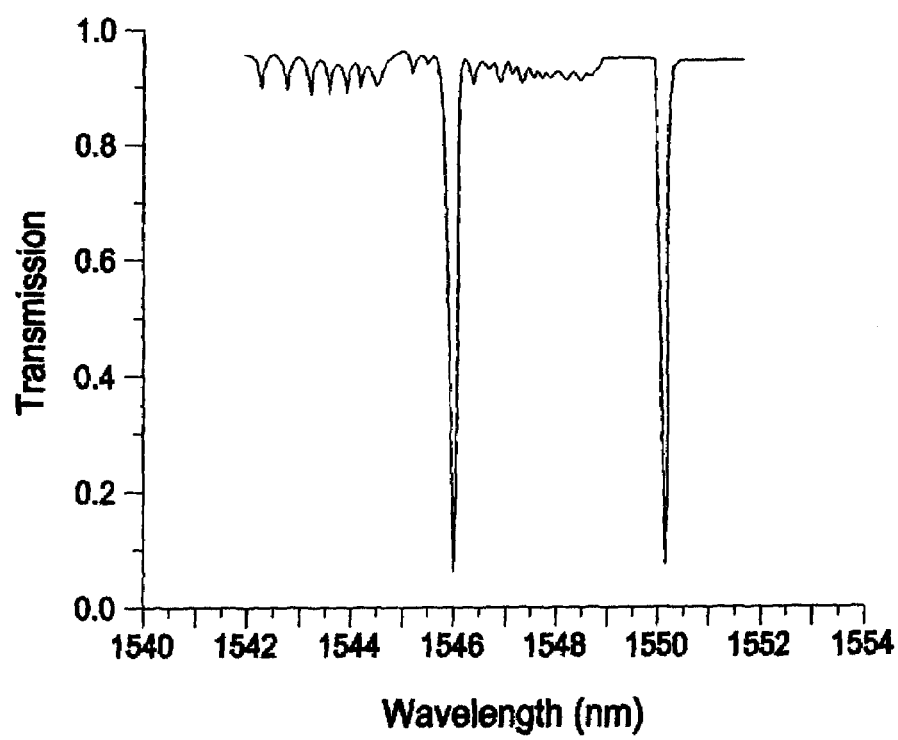
FIG. 6 is a graphical representation of transmission versus wavelength for a signal transmitted through the sensing module shown in FIG. 5.
Figure 7:
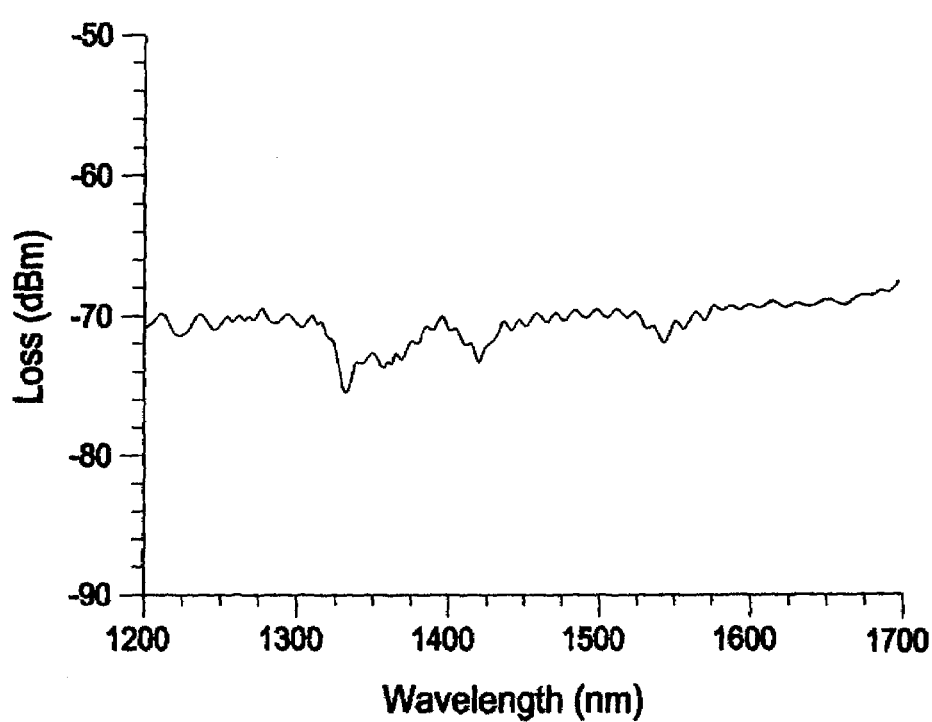
FIG. 7 is a graphical representation of power loss versus wavelength for a signal transmitted through the sensing grating element shown in FIG. 5.

Referring to FIGS. 5-7, in one embodiment, multi-functional sensing module 52, 53, 54, 55 and/or 56 is configured as a transmitive sensing module. In this embodiment, multi-functional sensing module 52, 53, 54, 55 and/or 56 includes a first short-period fiber grating 80 positioned about fiber core 64 and a second short-period fiber grating 82 positioned about fiber core 64 and at a distance along long axis 63 with respect to first short-period fiber grating 80. In a particular embodiment, first short-period fiber grating 80 and/or second short-period grating 82 includes a Bragg grating. As shown in FIG. 5, at least one long-aperiod fiber grating (LAG) 84 and/or at least one long-period fiber grating (LPG) 86 is positioned between first short-period fiber grating 80 and second short-period fiber grating 82. LAG 84 is suitable for environments wherein the temperature is at least about 500° C. and LPG 86 is suitable for environments wherein the temperature is less than about 500° C. Fiber cladding 66 is positioned about fiber gratings 80, 82, 84 and/or 86 and sensing skin 90 is positioned about fiber cladding 66.

Referring further to FIGS. 6 and 7, in one embodiment, sensing system 60 includes array 50 of multi-functional sensing modules for detecting the presence of a chemical gas, such as carbon monoxide (CO), and measuring a temperature within boiler 12, wherein a temperature within boiler 12 is greater than about 250° C. and a pressure within boiler 12 is greater than about 1000 psi. Array includes multi-functional sensing modules 52, 53, 54, 55 and 56 having two short-period gratings 80, 82 integrated with long-aperiod refractive index modulated grating 84 or long-period refractive index modulated grating 86. When broadband light is propagate through sensing modules 52, 53, 54, 55 and/or 56, two reflected peaks due to Bragg resonance are detected, as shown in FIG. 6. The wavelength shift of the two short-period fiber gratings is used to determine the local temperature. Further, the ratio of the Bragg peaks in the reflected power is used to detect the light loss in long-aperiod grating 84, as shown in FIG. 7, to measure the CO gas concentration, regardless of the high temperature and pressure. The temperature and the gas concentration can be detected at each spatial location with a corresponding multi-functional sensing module 52, 53, 54, 55 and/or 56.

Figure 9:
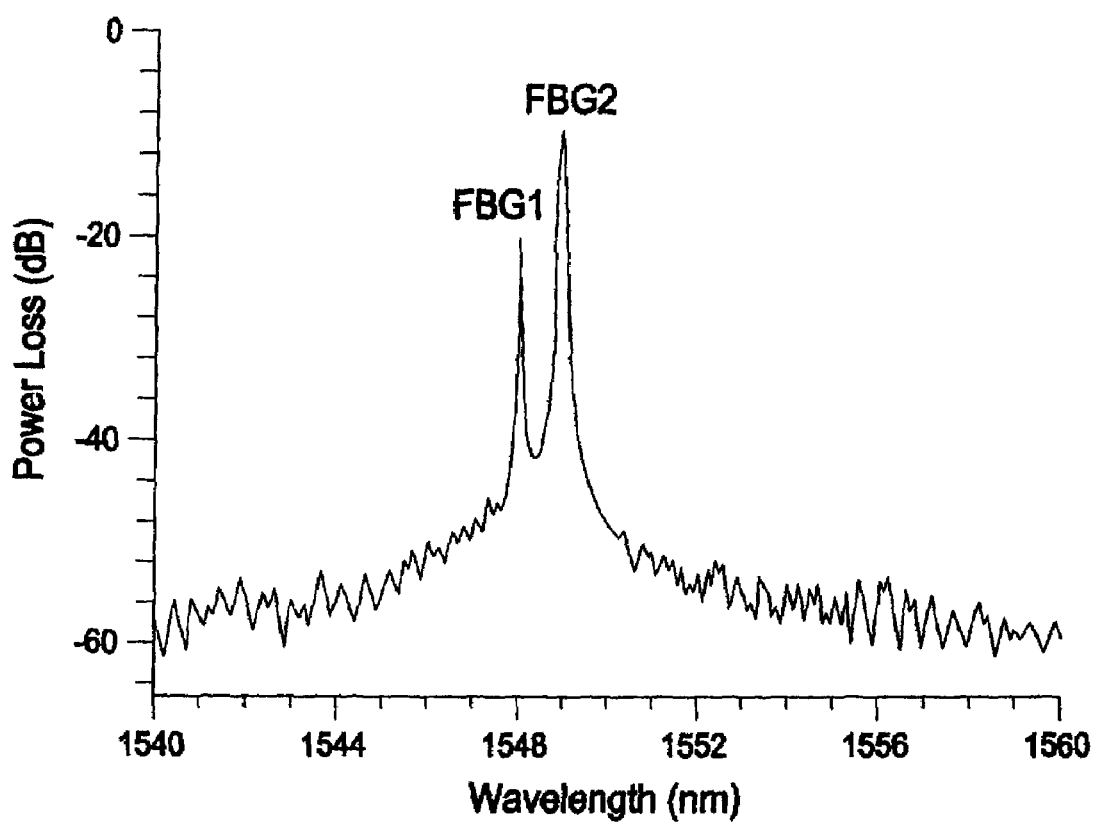
FIG. 9 is a graphical representation of power loss versus wavelength for a signal reflected by the sensing module shown in FIG. 8.
Figure 10:
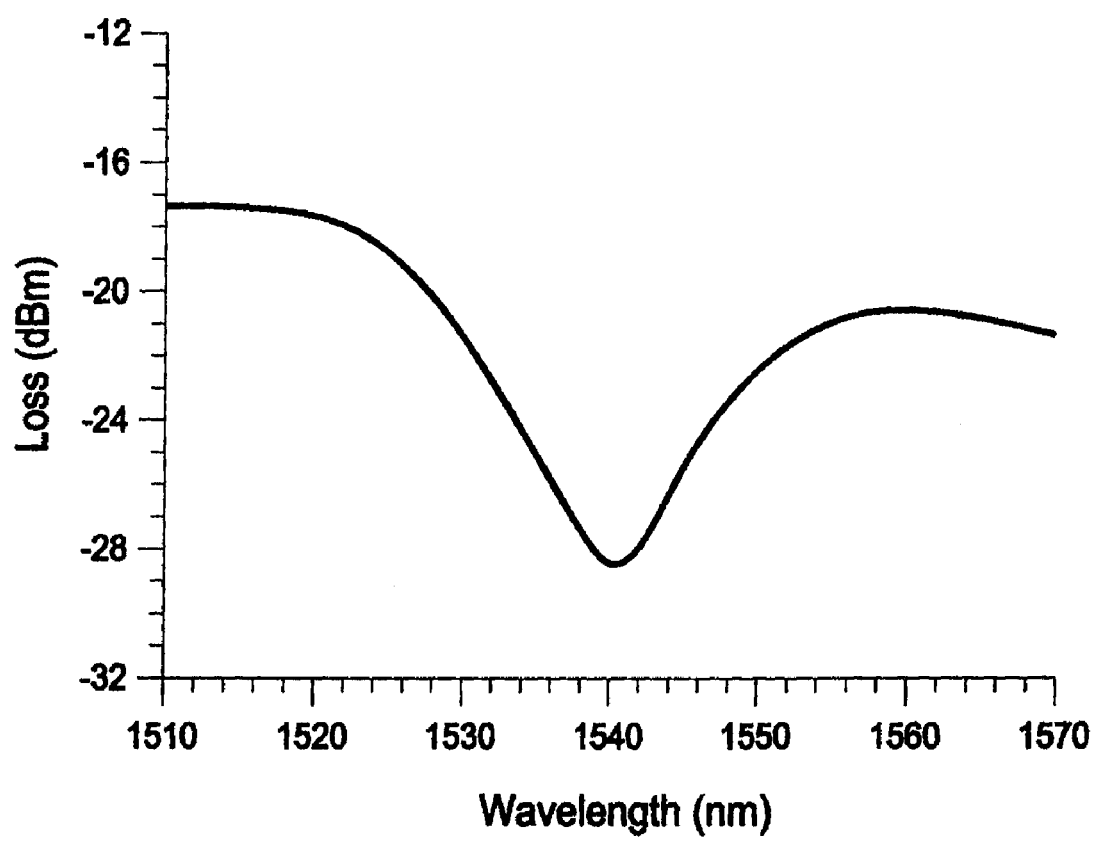
FIG. 10 is a graphical representation of power loss versus wavelength for a signal transmitted through the sensing grating between the fiber Bragg gratings shown in FIG. 8.

Referring to FIGS. 8-10, in one embodiment, multi-functional sensing module 52, 53, 54, 55 and/or 56 is configured as a reflective multi-functional sensing module. In this embodiment, multi-functional sensing module 52, 53, 54, 55 and/or 56 includes a reference reflector 92 positioned at an input end 94 of long-aperiod fiber grating (LAG) 84 or long-period fiber grating (LPG) 86 and a FBG reflector 96 positioned at an opposing output 98 of LAG 84 or LPG 86 or a corresponding input end of second short-period fiber grating 82. When broadband light is propagate through sensing modules 52, 53, 54, 55 and/or 56, two reflected peaks due to Bragg resonance are detected, as shown in FIG. 9. The wavelength shift of the two short-period fiber gratings is used to determine the local pressure. The ratio of the Bragg peaks in the reflected power is used to detect the light loss in long-period grating 86, as shown in FIG. 10, to measure the CO gas concentration, regardless of the high temperature and pressure. Referring to FIGS. 9 and 10, a power loss ratio between first short-period fiber grating 80 and second short-period fiber grating 82 determines the presence of a particular gas, such as CO, and the concentration of the gas at the location within boiler 12 where sensing module 52, 53, 54, 55 and/or 56 is located. The pressure and the gas concentration can be detected at each spatial location with a corresponding multi-functional sensing module 52, 53, 54, 55 and/or 56.

In one embodiment, sensing skin 90 includes a gas active nanoparticle material. In this embodiment, sensing skin 90 has a thickness that allows a few cladding modes propagation when a refractive index of sensing skin 90 is less than a refractive index of fiber core 64. Alternatively, sensing skin 90 has a thickness that allows a few radiation modes propagation when a refractive index of sensing skin 90 is greater than a refractive index of fiber core 64. Further, sensing skin 90 has a thermal expansion coefficient different from a thermal expansion coefficient of fiber cladding 66 such that a material induced interfacial strain is controlled. In a particular embodiment, the interfacial strain between sensing skin 90 and fiber cladding 66 is thermally compensated for by an athermal package and field calibration before system operation. In an alternative embodiment, optical fiber cable 62 is hermetical sealed with a hydrophobic membrane to protect the sensing modules and allow only gas penetration.

The present invention provides a method for monitoring operating conditions and/or parameters of power generating system 10 and coal boiler 12. In one embodiment, the presence of at least one gas emitted from coal boiler 12 is detected and/or monitored. A broadband light is propagated through optical fiber cable 62. Multi-functional sensing module 52, 53, 54, 55 and/or 56 reflects one wavelength of the broadband light and allows the remaining light to be transmitted through optical fiber cable 62. Referring to FIG. 7, a wavelength peak due to Bragg resonance is detected by first short-period fiber grating 80 and a wavelength peak due to Bragg resonance is detected by second short-period fiber grating 82. This shift in wavelength corresponds to a temperature within boiler 12 where sensing module 52, 53, 54, 55 and/or 56 is located. In one embodiment, the light loss is detected to measure the power loss ratio from first short-period fiber grating 80 and second short-period fiber grating 82. Referring to FIG. 9, a power loss ratio between first short-period fiber grating 80 and second short-period fiber grating 82 determines the presence of a particular gas, such as CO, and the concentration of the gas at the location within boiler 12 where sensing module 52, 53, 54, 55 and/or 56 is located. The temperature and the gas concentration can be detected by one multi-functional sensing module 52, 53, 54, 55 and/or 56.

The present invention provides a sensing system including an array of fiber optic multi-functional sensing modules that are capable of detecting the presence of a chemical gas, a temperature and/or a pressure at multiple spatial locations in a boiler environment, for example. The fiber optic multi-functional sensing modules include a fiber grating coated with a sensing skin including a chemical gas active nanomaterial. The nanomaterial has a nanoporous morphology having an average pore size less than about 2 microns, and the gas sensing performance is optimized in both response amplitude and response time. Further, the fiber sensing skin is selectively highly sensitive to chemical gases by doping the base material with a noble metal catalyst material. When a broadband light propagates through the sensing modules, two reflected peaks due to Bragg resonance are detected, and the ratio of the Bragg peaks in the reflected power loss is used to detect the light loss in the long-aperiod grating, regardless of the high temperature and pressure. The absorption and adsorption processes of the target gas modulate the coating film optical absorption properties and thereby cause a change in the index of refraction. This index of refraction change modulates the couplings among fundamental code mode, cladding modes and radiation modes. The associated propagation light loss in the sensing module will vary depending on the refractive index variation of the surrounding gas sensing material.

In one embodiment, the sensing skin includes an integration of nano-Pt/$SnO_2$ sensing material, for environmental temperatures less than about 400° C., and nano-Pd/Au/$Ga2O_3$ sensing material for environmental temperatures at least about 400° C., and long-aperiod/period fiber grating. The sensing skin includes a circumferentially coated thin film that functions as a CO gas sensor. Adsorbed oxygen and surface oxygen vacancies act as electron or hole trap states. The variations in oxygen vacancies result in a strong optical absorption, which varies the refractive index of the coated sensing material, and alters the light coupling between the fundamental mode and cladding modes, and the coupling between the cladding modes and radiation modes in the long-aperiod/period grating-cladding area. The two short-period Bragg gratings are embedded in the same environment as the long-aperiod/period grating. The ratio of the Bragg peaks is determined by the light loss properties of the long-aperiod/period grating, thereby providing a novel chemical gas-sensing module. Moreover, the wavelength shift of the two short-period fiber gratings is used to determine the local temperature. This simultaneous detection of localized temperature and gas emission has improved sensor performance and reduced low false positive rate, thereby providing an accurate measurement of the CO gas concentration, regardless of temperature variations and/or other spurious events.

The multi-functional sensing module allows distributed sensing capability for detecting multiple gases and multiple point temperature on the same fiber cable, which is suitable for real-time detection and monitoring in a boiler environment. The simultaneous sensing of temperature and CO gas emission serves to cost-effectively improve boiler efficiency and to reduce CO emissions. Further, the sensing system of the present invention is a passive operating system with no electric components or power requirements, and is intrinsically safe in hazardous areas that immunize electromagnetic interference and radio frequency interference.

While the invention has been described in terms of various specific embodiments, those skilled in the art will recognize that the invention can be practiced with modification within the spirit and scope of the claims.

What is claimed is:

1. A system for monitoring operating conditions of a power generating system, said system comprising:
   an optical fiber sensing cable extending through at least a portion of said power generating system, said optical fiber sensing cable having a core;
   an array of multi-functional sensing modules positioned along said optical fiber sensing cable, each multi-functional sensing module of said plurality of multi-functional sensing modules comprising a plurality of fiber gratings configured for monitoring at least one operating condition of said power generating system, wherein each multi-functional sensing module comprises at least one fiber grating coated with a sensing skin comprising a chemical gas active nanomaterial;

a broadband light source configured for emitting a light through said core; and an optical coupler in communication with said light source, said optical coupler configured for transmitting a portion of the light through said core and reflecting a portion of the light from the plurality of fiber gratings to a photodetector.

2. A system in accordance with claim 1 further comprising a computer in communication with said photodetector, said photodetector receiving a light signal from said array, and communicating a corresponding electrical signal to a computer.

3. A system in accordance with claim 1 wherein said nanomaterial comprises a plurality of nanoparticles having an average diameter of about 5 nanometers to about 10 nanometers.

4. A system in accordance with claim 1 wherein at least one multi-functional sensing module of said array is configured to detect a presence of at least one of $CO$, $CO_2$, $NO_x$, $O_2$, $H_2$ and $H_2S$.

5. A system for monitoring operating conditions of a power generating system, said system comprising:

an optical fiber sensing cable extending through at least a portion of said power generating system, said optical fiber sensing cable having a core;

an array of multi-functional sensing modules positioned along said optical fiber sensing cable, each multi-functional sensing module of said plurality of multi-functional sensing modules comprising a plurality of fiber gratings configured for monitoring at least one operating condition of said power generating system, wherein each multi-functional sensing module comprises two short-period fiber gratings and one of a long-aperiod fiber grating and a long-period fiber grating positioned between said two short-period fiber gratings;

a broadband light source configured for emitting a light through said core; and an optical coupler in communication with said light source, said optical coupler configured for transmitting a portion of the light through said core and reflecting a portion of the light from the plurality of fiber gratings to a photodetector.

6. A system for monitoring operating conditions of a power generating system, said system comprising:

an optical fiber sensing cable extending through at least a portion of said power generating system, said optical fiber sensing cable having a core;

an array of multi-functional sensing modules positioned along said optical fiber sensing cable, each multi-functional sensing module of said plurality of multi-functional sensing modules comprising a plurality of fiber gratings configured for monitoring at least one operating condition of said power generating system, wherein each multi-functional sensing module comprises a sensing skin having a sensing material comprising at least one of a nano-Pt/$SnO_2$ sensing material and a nano-Pd/Au/$Ga_2O_3$ sensing material;

a broadband light source configured for emitting a light through said core; and an optical coupler in communication with said light source, said optical coupler configured for transmitting a portion of the light through said core and reflecting a portion of the light from the plurality of fiber gratings to a photodetector.

7. A system for monitoring operating conditions of a power generating system, said system comprising:

an optical fiber sensing cable extending through at least a portion of said power generating system, said optical fiber sensing cable having a core;

an array of multi-functional sensing modules positioned along said optical fiber sensing cable, each multi-functional sensing module of said plurality of multi-functional sensing modules comprising a plurality of fiber gratings configured for monitoring at least one operating condition of said power generating system, wherein each multi-functional sensing module comprises a skin having a sensing material comprises at least one of $SnO_2$, $WO_x$, $Fe_2O_3$ and $Ga_2O_3$ doped with at least one of Pd, Pt, Au, Ag, Ni and CuO, a broadband light source configured for emitting a light through said core; and an optical coupler in communication with said light source, said optical coupler configured for transmitting a portion of the light through said core and reflecting a portion of the light from the plurality of fiber gratings to a photodetector.

* * * * *